United States Patent [19]

Dávid et al.

[11] Patent Number: 4,716,768
[45] Date of Patent: Jan. 5, 1988

[54] PROCESS AND APPARATUS FOR DETERMINING AND INFLUENCING THE FLOW PROPERTIES OF SOLID GRANULAR MATERIAL

[75] Inventors: Ágoston Dávid; János Pogány; László Rönkös, all of Budapest, Hungary

[73] Assignee: Richter Gedeon Vegyeszeti Gyar Rt, Budapest, Hungary

[21] Appl. No.: 922,783

[22] Filed: Oct. 23, 1986

Related U.S. Application Data

[63] Continuation-in-part of Ser. No. 818,080, Jan. 13, 1986, abandoned, which is a continuation of Ser. No. 755,204, Jul. 12, 1985, abandoned, which is a continuation of Ser. No. 549,204, Nov. 4, 1983, abandoned.

[30] Foreign Application Priority Data

Nov. 4, 1982 [HU] Hungary .................... 3545/82

[51] Int. Cl.$^4$ ............................................ G01G 11/00
[52] U.S. Cl. ...................................... 73/861; 177/50; 222/71; 364/510
[58] Field of Search ............... 73/223, 861, 3; 177/50; 222/55, 71; 364/510

[56] References Cited

U.S. PATENT DOCUMENTS

| | | | |
|---|---|---|---|
| 2,062,173 | 11/1936 | Haskins | 73/168 |
| 2,505,237 | 4/1950 | Dwyer | 73/223 X |
| 3,376,753 | 4/1968 | Pitkin et al. | 73/432 |
| 3,855,458 | 12/1974 | Motter et al. | 222/55 X |
| 4,144,943 | 3/1979 | Gallo | 177/50 |
| 4,458,539 | 7/1984 | Bilstad et al. | 73/861 |

*Primary Examiner*—Herbert Goldstein
*Attorney, Agent, or Firm*—Karl F. Ross; Herbert Dubno

[57] ABSTRACT

A process and apparatus for measuring the flow rate of solid granular material in which a sample holder of variable geometry is provided with an aperture containing a shutter. The aperture is opened and the material is collected and weighed. Either the time to collect a given weight or the weight collected in a given time is determined and combined with signals representing the sample holder geometry, aperture cross section and material constants to provide a measure of flow rate.

5 Claims, 2 Drawing Figures

PROCESS AND APPARATUS FOR DETERMINING AND INFLUENCING THE FLOW PROPERTIES OF SOLID GRANULAR MATERIAL

CROSS-REFERENCE TO RELATED APPLICATION

This application is a continuation-in-part application of the commonly owned copending application Ser. No. 818,080, filed Jan. 13, 1986, now abandoned, which is a continuation of Ser. No. 755,204, filed July 12, 1985, now abandoned, which is a continuation of Ser. No. 549,204, filed Nov. 4, 1983, now abandoned.

FIELD OF THE INVENTION

The invention relates to a process and apparatus with which flow properties of solid granular materials can be determined in a more versatile and reliable manner—compared to the prior art—either in course of the production of the materials or in the processing thereof. Production and processing, respectively, can also be influenced based upon the data determined by the process of the invention.

BACKGROUND OF THE INVENTION

The invention was developed for the determination of the flow properties of finely granular solid materials, i.e. powders, and will be described further in relation to this field of application. However, the invention is not at all restricted to granular materials of a given degree of fineness and for those skilled in art it will be quite obvious that the invention is also applicable to coarser granular materials, provided a sample holder can be prepared, through which these materials may pass under the same conditions as in technological devices conventionally applied for passing materials with coarser grains.

In all professional fields interested in powder-technology, in particular in the pharmaceutical industry and among others in the course of producing plant protecting agents, fodder, foodstuff, cosmetics and household goods, determination of flow properties of granular powders and influencing same by technological means is of utmost importance, in order to optimize transport, charging and compressing of powders and similar operations and processes, as well as to ensure proper quality of products.

Various powder flow measuring systems have been considered and several methods are known; however, neither a test method, nor an apparatus is known, which would enable determination of all parameters influencing flow properties and a control of process (technological optimalization) based on said properties. The known solutions are suitable for determination of only one part of the important characteristics determining altogether the process, and only this part can be considered for the controlling parameters. Accordingly by using the devices corresponding to the state of art, satisfactory optimization can be achieved only on the basis of empirical information.

The velocity of flow of certain powdery products discharged from a given tank has been examined thoroughly, however, only in dependence upon some important parameters. R. L. Brown and J. C. Richards (Trans. Inst. Chem. Eng. 38, 243; 1960) examined the role of the grain size of the powder and the diameter of the discharge aperture, taking into consideration the density of the grain too, but the empirical mathematical correlation explored by them contained more constants of unknown nature than the considered known parameters. This correlation can be applied in practice only with severe limitations.

Of the parameters influencing outflow velocity of powders the effects of the following different parameters were examined:

the effect of the height of the powder column and grain size (F. Q. Danish and E. L. Parrot: J. Pharm. Sci. 60, 548, 1971.);

effect of moisture content (D. J. Craik and B. F. Miller: J. Pharm. Pharmac. 10, 136T; 1958);

effect of grain size distribution and the diameter of the aperture, T. M. Jones and N. Pilpel: J. Pharm. Pharmac. 18, 429; 1966;

the minimal diameter required for outflow, the effect of grain size, grain density and geometry of grain shape, K. Kurihara, I. Ichikawa: Chem. Pharm. Bull. 21, 394; 1973.

All of these examinations were performed with equipment which was provided with a powder tank with a discharge opening having changeable diameter (generally the change does not mean any optional change of the aperture diameter within a fixed range, but switching over between the closed and open state, independently of whether closing and opening could be performed for one single value of the diameter or with the exchangeability of the structural element containing the discharge aperture according to a size order). We shall use the definition "it can be opened and closed" instead of the attribute "changeable." In the course of measuring a so-called "Flowometer" was used, which was provided with an agitator, as well as an instrument suitable for measuring the shearing force. All these devices are suitable for determining only one group of the parameters to be considered and to define the empirical correlations between said preferential parameters.

From our earlier Hungarian Patent HU-PS No. 174 116 a solution is known which ensures advantageous apparatus or technical conditions for the determination of flow properties of solid granular materials with the simultaneous observation of different characteristics; this approach enables the application of a process, comprising keeping two characteristics out of three always constant and measuring the third parameter as an independent variable. The data obtained from the mass of facts by mathematical analysis are suitable for the determination of the data serving as a starting point for the optimization of production or processing. This technique enables an analysis only starting from variables of restricted number.

OBJECT OF THE INVENTION

The object of our invention is to develop a measuring method and an apparatus, whereby a quantitative correlation can be established between all important parameters influencing the flow properties of granular powders by one single mathematical formula.

SUMMARY OF THE INVENTION

As in our system (see the aforementioned Hungarian patent), the sample is placed in sample holder, preferably of the shape of a funnel, the discharge aperture of which can be opened and closed, respectively, and which can be controlled in two modes of operation (mass-proportional or time-proportional); thereafter, by changing some parameters of the outflow of the medium (size of the aperture, duration etc.) in the respective cycles, we produce—through the set of cycles—signals representing the constant parameters, and the values of parameters changing in the single cycles respectively. The signals are forwarded to the proper inputs of the evaluating unit, while the result signals produced by the evaluating unit are displayed and/or recorded and/or read.

In the course of the process of the invention, the afore summarized general characteristics have been maintained, and can be considered as common family-characteristics of our earlier solution and the new invention.

The difference between our earlier process and the process according to the present invention lies in that while the samples are permitted to pass, through the sample receptacle, data signals are produced, from which based upon a newly discovered correlation developed below, further data signals representing all important parameters can be directly derived.

In the process according to the invention an exchangeable set of sample holders with different geometric parameters (receiving equal sample quantities at different column heights) was used, and prior to the start of each measuring cycle, the sample medium is filled into the sample holder, whereafter a signal representing the type of the sampel holder (geometrical characteristics) and a signal representing the size of the discharge aperture are produced; thereafter the signals are led to the proper inputs of the signal processing unit, the desired mode of operation is set and the signal representing the chosen mode of operation is also led to the proper inputs of the signal processing unit. In case of a mass-proportional mode of operation, the signal representing a pre-selected mass of sample medium is also applied to the appropriate input of the signal processing unit.

In case of a time-proportional mode of operation, according to one version, a signal representing a preselected span of time is applied to the suitable input of the signal processing unit, while according to an improved version, the reference span of time is not pre-signalled to the signal processing unit, but in each measuring cycle the actual span of time, being close to the chosen span of time but slightly differing from time to time is controlled and the signal representing it is applied to the proper inputs of the signal processing unit.

Thereafter the discharge aperture is opened and depending on the mode of operation we proceed as follows:

in case of the mass-proportional mode of operation we follow the outflow of the sample from the sample holder and at the moment when the sample holder is empty the signal representing the full span of time of discharge is produced and applied to the corresponding input of the signal processing unit.

In case of the time-proportional mode of operation the aperture is closed after the expiration of the span of time prescribed for the given measuring cycle, the signal representing the mass of the discharged sample medium is produced and applied to the proper input of the signal processing unit, thereafter the signal processing unit is programmed according to the equation arranged for the dependent variable we are searching for, the signal appearing on the result output is displayed and/or recorded and/or read, and if desired the result signal or a signal derived therefrom is applied to the control inputs of the intervening devices modifying the parameters of the process.

Signal processing is advantageously controlled according to one of the correlations as deduced below:

The apparatus according to the invention is preferably used for carrying out the process. Considering the various means available in the field of modern measuring technics, automation and in particular in the field of process control and electronic digital data processing, it goes without saying that the process can be carried out by means of differently designed or coupled intervening devices. General purpose measuring technical and process controlling systems may be used, if the field of application includes the fulfillment of the tasks of such devices developed expressly for the process according to the invention, which can be inserted into known activating and signal processing systems serving simultaneously for several other processes at the corresponding place. Even when using such general purpose devices the system prepared for said purpose prior to performing the process will have the general characteristics described hereinafter.

The apparatus of the invention comprises a sample holding receptacle, the discharge aperture of which can be closed and opened, respectively, with a blocking (closing) element fitted to the discharge aperture of the sample holder and an intervening element for the actuation thereof, and a control and evaluating unit.

More specifically, the apparatus of the invention is provided with a set of exchangeable sample holders with identical volumetric capacities with different geometrical parameters (while the value of "cross-section x height" is constant the values of each of these factors can be varied) or is provided with one single sample holder with changeable geometry with a set of exchangeable sample holding inserts fitted thereto. To the corresponding points of the sample holder a type signal transmitter and an aperture signal transmitter are connected, below the discharge aperture of the sample holder a mass signal-transmitter, preferably a balance, is arranged, while the evaluating unit is represented by an electronic signal processing unit, to the inputs of which the type-signal transmitter, aperture-signal transmitter, period-signal transmitter, mass-signal transmitter and means for observing the path are connected.

The output signal of the type-signal transmitter is the type signal for the sample holder (insert) or the exchangeable sample holders (inserts) used in the given measuring phase, delivering the information to the signal processing unit about the column height and the volumetric measure to be realized thereby.

The aperture-signal transmitter gives an output signal representing the useful cross-section of the discharge aperture.

The period-signal transmitter gives a signal representing the instant (open, closed) position of the aperture-closing organ, the alternations of which deliever the start and stop signals, respectively, for performing time measuring in the time-signal transmitter or in the signal processing unit.

The device provided with suitably selected detectors (optical, capactivie etc.) for observing the path, observes the advance of the material in the discharge channel, i.e. it delivers the state-changing phase-times needed for the derivation of the quantity to be measured (period of flow) for the mass-proportional mode of operation.

The mass-signal transmitter—used in our earlier system—is preferably a balance, the output signal of which represents the mass flow of the sample medium during the reference period chosen in the time-proportional mode of operation and accumulated on the balance. Even in case of a preselected reference period, the period can be transmitted to the signal processing unit in different ways. In certain measuring processes it may be sufficient to give the signal processing unit the nominal period as a selected parameter, in this case a period-signal transmitter set to a constant value is used. However, if it is not intended to perform processing related to the nominal period, because thus the desired accuracy can not be obtained, the period signal will be delivered by the previously mentioned period-signal transmitter, which directly monitors the span of time of the open state. When reference to the nominal value is not sufficient, the effective value of the sample mass can be observed as well.

BRIEF DESCRIPTION OF THE DRAWING

The invention will be explained in detail with reference to the accompanying drawing in which.

DESCRIPTION

Figure 1:
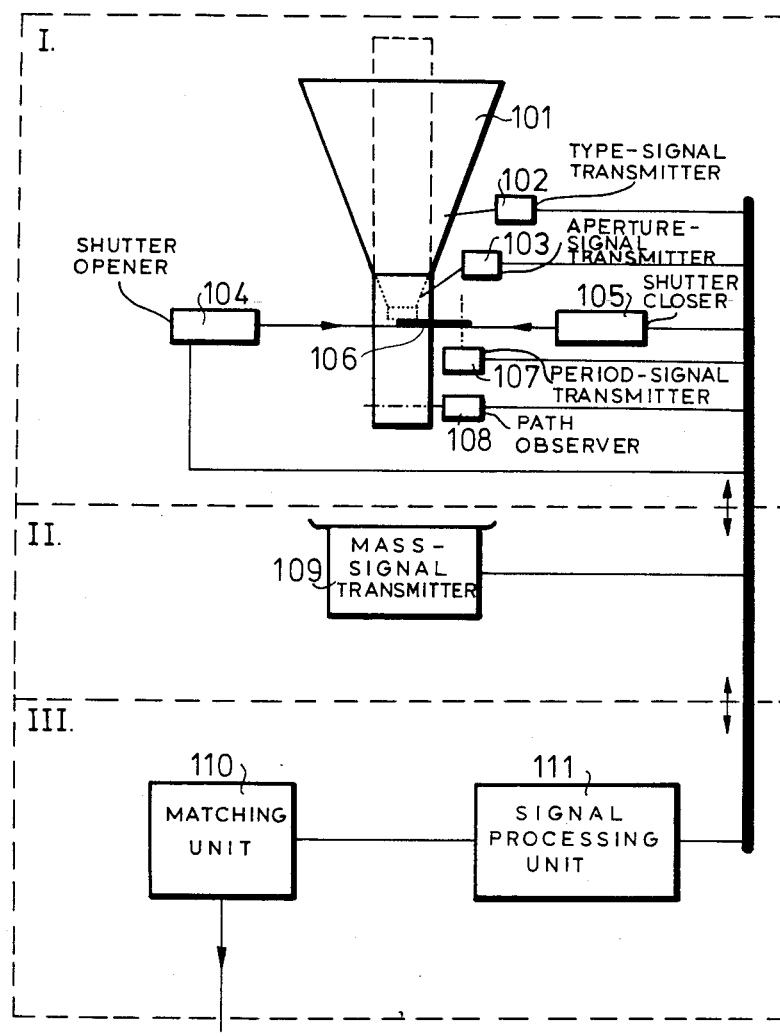
FIG. 1 is a block diagram of the apparatus according to the invention.

As can be seen from FIG. 1, the set of devices forming the apparatus can be divided into three main functional parts. The main part I comprises the sample holder 101 with the changeable geometry and the devices for partly observing, partly influencing the state thereof, namely the type-signal transmitter 102, the aperture-signal transmitter 103, the first aperture actuating element 104, the second aperture actuating element 105, the aperture-closing element 106, the period-signal transmitter 107 and the device 108 observing the path. The main part II is formed by the mass-signal transmitter 109, generally a balance. The main part III is formed by the signal processing unit 111 and the matching unit 110 connected thereto. With the embodiment serving as an example, a sample holder as recommended in industrial standards is used, with an angular subtense of 40°, with an aperture advantageously changeable in the range between 0.3 and 1.5 cm, and which can be increased in height by using a cylindrical insert. The aperture-signal transmitter informs the signal processing unit of the size of the aperture, while the type-signal transmitter 102 indicates the type of the sample holder 101 used for the test. The device 108 observing the path observes the discharge aperture and informs the signal processing unit whether the sample medium is passing through or not.

The first and second elements 104, 105 provide for opening and closing, respectively, of the aperture-closing element 106. The mass-signal transmitter 109 is preferably an electronic balance delivering an output signal representing the weighed mass. The signals of the different signal transmitters and the signals representing the different reference values are processed in the signal processing unit 111, the result output is represented by the matching stage 110 (FIG. 1).

Figure 2:
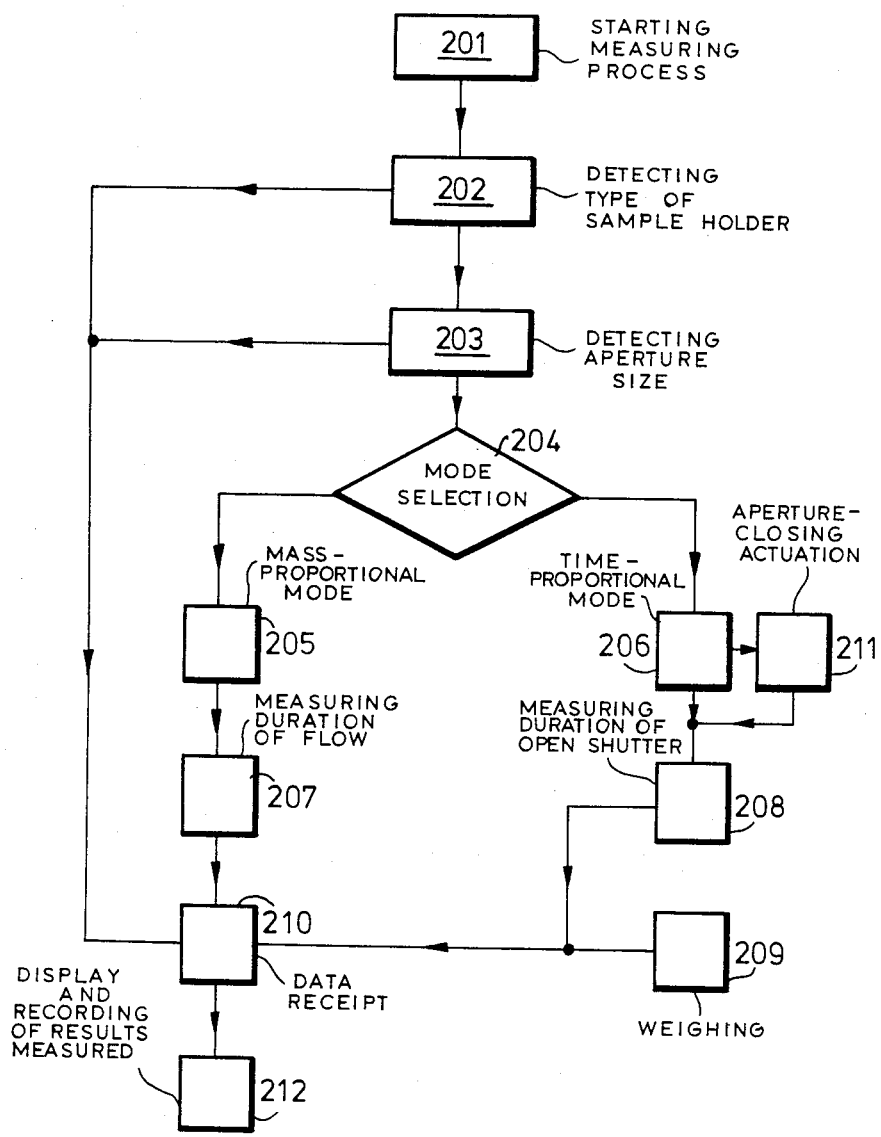
FIG. 2 is a flow diagram of a preferred performance of the flow process according to the invention.

Operation of the equipment is illustrated by the information flow diagram FIG. 2. The sample of the material to be examined is put into the sample holder 101. The corresponding signal transmitters forward information to the signal processing unit 111 on the type of the used sample holder and the height of the sample column depending on the use of the inserts, respectively, as well as the size of discharge opening. Thereafter the mode of operation is selected. In case of a mass-proportional mode of operation the device 108 observing the path informs the signal processing unit 111 about the span of time, during which the nominal mass of the sample medium, has passed the discharge aperture. This can also be achieved as follows: the device 108 observing the path can be a simple two-state structural element and by means of the signals representing the change in state in one or in the other direction as signals giving the starting and final phase, the signal processing unit 111 itself determines the duration of through-flow so that the device 108 does not indicate the state change but delivers a signal representing the span of time passed between the two state changes. In case of time-proportional mode of operation the mass-signal transmitter 109 delivers the signal representing the mass passing during the time unit by a method known per se.

The signal processing unit 111 processes the data-signals received from the different signal-transmitters depending on the selected mode of operation and in accordance with the operation of chain of actions connected according to the algorithm ensuring the production of the quantity sought and thereafter it displays, records the result signals and forwards these or those derived from the result signal to the corresponding input of the process controlling instrument.

The meanings of the steps illustrated in FIG. 2 are as follows:
- 201: starting the measuring process
- 202: signal generation for the type of the funnel, the height of the sample column,
- 203: signal generation for the size of the discharge aperture
- 204: selection of the mode of operation
- 205: mass-proportional mode of operation
- 206: time-proportional mode of operation
- 207: determination of the duration of the outflow in the mode 205 of operation
- 208: determination of the duration of the open state in the mode 206 of operation
- 209: weighing
- 210: receipt of data, control, calculation
- 211: actuating the aperture-closing element
- 212: forwarding of the result signals/displays, recording, intervention/.

The process and the apparatus according to the invention enable the examination of solid granular materials, preferably by weighing the mass passing through the cross-section during the time unit, expressed by the formula:

$$m/t \, [g \cdot s^{-1}];$$

by weighing the density of mass flow: the mass m passing through the cross-section unit A during the time unit t, expressed by the formula:

$$m/t \cdot A \, [g \cdot s^{-1} \cdot cm^{-2}].$$

Duration of outflow of a sample of given mass can be measured in the mass-proportional mode of operation, and by using the signals derived from the data-signals representing the result of measuring system characteristics can be optimized within wide limits, including constants relating to mass and/or time for the aperture size, for the grain-size, grain-density or grain-size-distribution (apparent density of the grain aggregate), or even factors relating to the shape of the grains.

The time-proportional mode of operation can be advantageously used for testing the physical characteristics of solid granular press materials, granulate-compositions and/or the regulation, optimization of the production of pressed materials. As a further advantageous field of application, the finishing technology in the pharmaceutical industry can be mentioned.

As already mentioned before, examinations for the same purposes have been performed—according to the state of art—on samples, the important characteristics of which (grain-diameter, grain density, grain size-distribution) differ only to a slight extent; as a consequence, the examinations did not enable a simultaneous comprehensive mathematical analysis of the characteristic parameters. The advantages of the invention are confirmed by the results of the tests performed on the samples, reported in Table 1.

| No. | Material | $d_s$ | $\rho_s$ | $\rho$ | $d_{omin}$ |
| --- | --- | --- | --- | --- | --- |
| 1. | Lactose pellet | 0.095 | 1.42 | 0.74 | 0.5 |
| 2. | Lactose pellet | 0.068 | 1.43 | 0.76 | 0.4 |
| 3. | Lactose pellet | 0.055 | 1.44 | 0.77 | 0.4 |
| 4. | Poppy | 0.1 | 1.16 | 0.61 | 0.4 |
| 5. | Mustard-seed | 0.196 | 1.7 | 0.76 | 0.7 |
| 6. | Glass pearl | 0.322 | 2.47 | 1.52 | 1.2 |
| 7. | Glass pearl | 0.409 | 2.47 | 1.43 | 1.2 |
| 8. | Lead shot | 0.162 | 11.4 | 6.33 | 0.6 |

In the table, $d_s$ stands for the average diameter of the grain in cm, $\rho_s$ for the grain or bulk density weighed by using the pyonometric method, expressed in g.cm$^{-3}$, $\rho$ stands for the apparent density of the grain aggregate expressed in g.cm$^{-3}$ and $d_{omin}$ refers to the minimal diameter of the aperture in cm, if the aperture is smaller, then $d_{omin}$ mass flow can not be measured.

Lactose pellets were produced in a plant with starch and polyvinyl-pyrrolydone as additives. The granular fractions separated in a sieve fell into the range 1.0–0.9, 0.7–0.63 and 0.63–0.5 mm, while average grain diameter $d_s$ was determined on basis of mass-proportion. For performing examination in time-proportional mode of operation a material sample of the mass of 40 to 100 g is placed into the sample holder 101, whereafter the mass of the outflowing sample-medium, flowing through discharge openings of various diameters ($d_o$ = 0.3 to 1.5 cm) in each cycle is weighted at ten different spans of time. The series were repeated three times, and the standard deviation ($\pm \delta \%$) of 30 measuring characterized the accuracy of test method.

Mass-flow Q and density of mass-flow Q/A thus determined are summarized in Table 2.

TABLE 2

| No. of the sample | $\pm \delta \%$ | Q Q/A | $d_o$ | | | | | | | | |
| --- | --- | --- | --- | --- | --- | --- | --- | --- | --- | --- | --- |
| | | | 1.2 | 1.1 | 1.0 | 0.9 | 0.8 | 0.7 | 0.6 | 0.5 | 0.4 |
| 1. | 4.1 | Q | 19.82 | 15.8 | 12.3 | 9.62 | 6.50 | 4.45 | 2.78 | 1.80 | — |
| | | Q/A | 18.7 | 17.04 | 16.76 | 15.27 | 13.8 | 12.5 | 10.6 | 10.06 | — |
| 2. | 1.2 | Q | 20.97 | 16.8 | 13.2 | 10.17 | 6.75 | 4.70 | 3.12 | 1.96 | 0.80 |
| | | Q/A | 19.78 | 18.98 | 17.98 | 16.87 | 14.33 | 13.17 | 11.86 | 10.95 | 7.08 |
| 3. | 2.4 | Q | 21.15 | 17.15 | 13.3 | 10.57 | 6.86 | 4.75 | 3.19 | 1.97 | 0.85 |
| | | Q/A | 29.95 | 19.38 | 18.12 | 17.53 | 11.56 | 13.9 | 12.13 | 11.05 | 7.52 |
| 4. | 3.6 | Q | 16.33 | 13.3 | 10.4 | 7.83 | 5.67 | 3.59 | 2.28 | 1.42 | 0.64 |
| | | Q/A | 15.41 | 15.03 | 14.17 | 12.99 | 12.04 | 10.06 | 8.67 | 7.93 | 5.66 |
| 5. | 2.1 | Q | 17.45 | 13.55 | 10.1 | 7.12 | 5.30 | 3.30 | — | — | — |
| | | Q/A | 16.46 | 15.31 | 13.76 | 11.81 | 11.25 | 9.20 | — | — | — |
| 6. | 4.5 | Q | 25.55 | 18.23 | — | — | — | — | — | — | — |
| | | Q/A | 22.61 | 20.6 | — | — | — | — | — | — | — |
| 7. | 3.8 | Q | 24.75 | 18.49 | — | — | — | — | — | — | — |
| | | Q/A | 21.9 | 20.9 | — | — | — | — | — | — | — |
| 8. | 3.2 | Q | 212.9 | 162.0 | 121.0 | 86.32 | 66.59 | 44.3 | 28.24 | 20.08 | — |
| | | Q/A | 200.8 | 183.1 | 164.9 | 143.2 | 141.4 | 124.3 | 107.3 | 112.2 | — |

Analyzing the data thus obtained we have found that by the values of mass-flow Q and density of mass-flow Q/A new function-correlations can be set up, and some of the demanded characteristics can be derived from said quantities. So e.g. the correlation between Q mass-flow, the average size diameter $d_s$ and aperture-diameter $d_o$ can be expressed by the following n-th degree espression:

$$Q_m = \frac{m}{t} = k_1 \frac{Q_s}{d_s} (d_o - D_m)^n \times (d_o^n - k_2 d_o + k_3) \quad (1)$$

wherein: k; $k_2$; and $k_3$ are constants characterizing material quality. $D_m$ restricts the ratio $d_o$ and $d_s$; $D_m \geq 3 d_s$ as a practical condition; $D_m$ = minimal aperture-diameter.

At the same time, density of mass-flow Q/A can be correlated to the parameter-spectrum determining flow behavior of solid granular powders according to the following general expression:

$$Q/A = f(d_s, d_o \rho_s \rho, g, j, G) \quad (2)$$

wherein the definition of the new symbols is as follows: g = gravitational acceleration constant, j = factor of rolling-sliding resistance, G = a constant characterizing material quality and simultaneously representing a geometric factor.

An example for the optimization of the technology of a granulate to be pressed to tablets can be found hereinafter.

According to an empirical solution of the function (2)

$$Q/A = \delta_s \cdot j \cdot \left( \frac{d_o^2}{d_s} \right) \times G \cdot g \cdot \left( 1 - \frac{\rho_s - \rho}{\rho_s \cdot \rho} \right) \quad (3)$$

By the aid of the function (3) constants j and G can be derived from the measured data for a known granulate and taking these into consideration optimal parameters of the granulate under consideration can be calculated within reasonable limits.

Relative comparison is demonstrated by the test results data of the samples of table 1.

TABLE 3

| Sample | $r^2$ | j | G |
|---|---|---|---|
| Lactose pellet 0.095 | 1.00 | 0.56 | 0.838 |
| Lactose pellet 0.068 | 0.98 | 0.42 | 0.790 |
| Lactose pellet 0.055 | 0.97 | 0.35 | 0.768 |
| Poppy | 0.97 | 0.66 | 1.147 |
| Mustard-seed | 0.98 | 0.87 | 0.910 |
| Lead shot | 0.98 | 1.12 | 1.016 |

In the above table $r^2$ stands for a regression coefficient. The data show that the coefficient j increases mainly with increasing grain density (in particular in the case of lead-shot), unevennesss of the grain surface (in particular in case of poppy and mustard-seed), i.e. the rolling-sliding resistance increases, the constant G is increased by the apparent density of the grain aggregate (including grain-size-distribution), as well as by grain density (in particular in case of lead-shot, but also in case of mustard-seed). Geometry of poppy is ellipsoid and not spherically symmetrical, the value of the constant G is sensitive also to said geometry.

Accordingly, a granulate-composition to be optimalized is prepared with different composition, moisture content and eventually by using various technological processes. Thereafter the mass-flow Q and density of mass-flow Q/A values of the experimental sample-series are measured according to the invention.

For the tablets to be produced of diameter $d_o$ and of mass m—by using the formula m=Q.t the time t, can be obtained which is needed for filling the die. The tabletting equipment can be chosen accordingly.

If no granulate with suitable mass-flow can be found in the series of samples, then by the aid of the density of mass-flow values Q/A calculated for the different aperture-diameters on basis of the formula (3) the parameters $d_o$, $d_s$, $\rho_s$, and $\rho$ adapted to the optimally lowest constants j and G can be determined.

The optimal parameters are then ensured in the course of granulate production by using the known technological methods—not empirically.

As already mentioned before, the time-signal transmitter is not necessarily the time-signal transmitter 107 sensing directly actual span of time of the open state. If measuring accuracy is satisfactory by considering the selected nominal span of time, the time-signal transmitter might be a signal source set to the nominal value, so the equipment will be provided only with such a device, (the signal source may even form a part of the signal processing unit, either in the form of software, or hardware). It may happen that the period-signal transmitter 107 which can be seen in FIG. 1, is able to ensure desired accuracy with a corrector only. The period-signal transmitter 107 has a position-signal transmitter being sensitive to the two final positions of the aperture-closing organ 106, which—after having reached one or the other final position—generates an output pulse representing the change of state (change of state in direction of closing or opening). If the signal processing unit 111 is used for generating the signal representing the span of time between the points of time of the two changes in state, the period-signal transmitter 107 consists only of the position-signal transmitter delivering the two state-signals needed for the derivation of the span of time. In another embodiment the period-signal transmitter 107 is designed so as to give an output signal representing directly the span of time.

However, in both embodiments this type of signal formation will give an accurate value only, if the transients of the displacement between the two extreme positions of the aperture-closing organ 106 are the same in both senses (if through the gradually widening or narrowing aperture the medium is allowed to pass). If the specific transmission values of the transient in the closing respectively, in the opening direction are not equivalent values, transient process is to be followed with the sensors. This can be performed so, that the period-signal transmitter 107 consists only of the sensors observing the transient and the signal processing unit 111 generates the period-signal taking the signals of the two extreme positions and the transient signal as a basis or on basis of the two state-signals and the transient signal the time-signal transmitter 107 generates the signal representing directly the periods, which is then led into the signal processing unit 111.

Changing of the geometry of the sample holder 101 can be realized in several ways. From the point of view of construction it seems to be the most simple solution to prepare a set of sample holders with different column heights and discharge apertures; these can be inserted into a suitable place within the apparatus. The changeable set of elements, however, is of a large volume. A smaller volume can be obtained, if in one common funnel insert elements modifying the geometry are placed.

In further preferred embodiment below the lower aperture of the funnel a disc is rotated in a stepping mode of operation which is formed with a set of permeable apertures with different cross-sections. In this embodiment the sample holder is formed as a funnel-shaped body, below the lower aperture of which a disc is arranged, which can be rotated excentrically to the central axis of the funnel and along the peripheral arc of the disc intersecting the central axis of the funnel permeable openings are formed with different cross-sections one after the other, while the element of the disc enabling the stepping motion is provided with a blocking organ; the blocking positions occupy an angular position, in which one of the apertures allowing passing through the sample covers the lower aperture of the funnel.

We claim:

1. A process for determining flow properties of solid granular materials, comprising the steps of:
    (a) selectively positioning a funnel-shaped sample holder with selected geometry at least in terms of a selected height in a position to receive a sample of solid granular material;
    (b) selectively disposing an aperture of selected flow cross-section below said sample holder;
    (c) opening a passage for said sample holder through said aperture;
    (d) collecting the sample traversing said aperture in a balance;
    (e) generating a type signal representing the selected geometry of said sample holder;
    (f) generating an aperture signal representing the cross section of the selected aperture;
    (g) generating a flow-initialing signal upon the opening of communication through said aperture;
    (h) selecting between a first measuring mode in which a mass-proportional measurement is made and a second measuring mode in which a time-proportional measurement is made so that:

(h₁) upon selection of said first measuring mode a signal proportional to the mass flow of said sample is generated at said balance, and (h₂) upon selection of said second mode a signal is generated upon termination of flow through said aperture;

(i) applying said signals to a signal processing unit and automatically determining therein from the signals applied thereto a value Q and a value Q/A where $$Q = \frac{m}{t} = k_1 \frac{\rho_s}{d_s} (d_o - D_m)^n \cdot (d_o^n - k_2 d_o + k_3)$$

and $$Q/A = \rho_s \cdot j \cdot \frac{d_o^2}{d_s} + G \cdot g \cdot \left(1 - \frac{\rho_s - \rho}{\rho_s \cdot \rho}\right)$$

wherein Q is a measured flow rate of said sample through said aperture, m is the measured mass of said sample, t is the time during which flow occurred, $k_1$, $k_2$ and $k_3$ are empirically derived constants relevant to said material and determined by passage of a material with given properties through said aperture and changing said aperture for successive tests, $D_m$ is a minimum aperture size such that $D_m \geq 3d_s$, $d_s$ is the average grain size, $d_o$ is a measure of aperture diameter, $\rho_s$ is the density of the solid granular material, A is a known cross section of a particular aperture, g is the gravitational acceleration constant, j is a coefficient of rolling-sliding substance, G is a coefficient of material quality representing granule shape and $\rho$ is the virtual density of the aggregated material, coefficients j and G being determined by passage of a material with given properties through said aperture changing said aperture for successive tests; and (j) outputting at least one result signal representing at least one of flow properties of said sample by the processing of the signals applied to said unit in accordance with at least one of the relationships for Q and Q/A, respectively.

2. The process defined in claim 1 wherein a result signal from step (j) is applied to a granulating apparatus to control the filling of tabletting die.

3. An apparatus for automatically determining flow properties of a granular solid material comprising:

a variable geometry sample holder having a selected height for a sample of granular material to be received therein;

means for positioning an aperture of selected cross-sectional area below said holder so as to be traversed by a gravitational flow of said sample;

a closure element blocking said flow in one position and permitting said flow in another position;

a balance below said aperture for receiving said flow;

a type-signal generator connected to said sample holder for generating a type signal representing the selected geometry of said holder;

an aperture-signal generator connected to said aperture for generating a signal representing the cross section of said aperture;

means connected to said element for generating a signal representing the inception of flow of said sample through said aperture;

means connected to said balance for generating a signal representing the mass of said sample collected by said balance;

means for selecting between a first mode for mass-proportional measurement and a second mode for time-proportional measurement;

means effective in at least one of said modes and responsive to said flow for generating a signal representing a time of termination thereof;

a signal processing unit connected to receive all of said signals and provided with a transfer function in accordance with at least one of the relationships:

$$Q = \frac{m}{t} = k_1 \frac{\rho_s}{d_s} (d_o - D_m)^n \cdot (d_o^n - k_2 d_o + k_3)$$

and $$Q/A = \rho_s \cdot j \cdot \frac{d_o^2}{d_s} + G \cdot g \cdot \left(1 - \frac{\rho_s - \rho}{\rho_s \cdot \rho}\right)$$

wherein Q is a measured flow rate of said sample through said aperture, m is the measured mass of said sample, t is the time during which flow occurred, $k_1$, $k_2$ and $k_3$ are empirically derived constants relevant to said material and determined by passage of a material with given properties through said aperture and changing said aperture for successive tests, $D_m$ is a minimum aperture size such that $D_m \geq 3d_s$, $d_s$ is the average grain size, $d_o$ is a measure of aperture diameter, $\rho_s$ is the density of the solid granular material, A is a known cross section of a particular aperture, g is the gravitational acceleration constant, j is a coefficient of rolling-sliding substance, G is a coefficient of material quality representing granule shape and $\rho$ is the virtual density of the aggregated material, coefficients j and G being determined by passage of a material with given properties through said aperture changing said aperture for successive tests; and output means connected to said signal-processing unit for generating an output signal representing a parameter of the material of said sample determined in accordance with a selected one of said relationships.

4. The appparatus defined in claim 3 wherein said output means include means for displaying and recording parameters of said sample used in the determined by said relationship.

5. A process for controlling a filling apparatus in accordance with flow properties of solid granular materials, comprising the steps of:

(a) selectively positioning a funnel-shaped sample holder with selected geometry at least in terms of a selected height in a position to receive a sample of solid granular material;

(b) selectively disposing an aperture of selected flow cross section below said sample holder;

(c) opening a passage for said sample holder through said aperture;

(d) collecting the sample traversing said aperture in a balance;

(e) generating a type signal representing the selected geometry of said sample holder;

(f) generating an aperture signal representing the cross section of the selected aperture;

(g) generating a flow-initiating signal upon the opening of communication through said aperture;
(h) selecting between a first measuring mode in which a mass-proportional measurement is made and a second measuring mode in which a time-proportional measurement is made so that:
  (h$_1$) upon selection of said first measuring mode a signal proportional to the mass flow of said sample is generated at said balance, and
  (h$_2$) upon selection of said second mode a signal is generated upon termination of flow through said aperture;
(i) applying said signals to a signal processing unit and automatically determining therein from the signals applied thereto a value Q and a value Q/A where $$Q = \frac{m}{t} = k_1 \frac{\rho_s}{d_s}(d_o - D_m)^n \cdot (d_o^n - k_2 d_o + k_3)$$

and $$Q/A = \rho_s \cdot j \cdot \frac{d_o^2}{d_s} + G \cdot g \cdot \left(1 - \frac{\rho_s - \rho}{\rho_s \cdot \rho}\right)$$

wherein Q is a measured flow rate of said sample through said aperture, m is the measured mass of said sample, t is the time during which flow occurred, $k_1$, $k_2$ and $k_3$ are empirically derived constants relevant to said material and determined by passage of a material with given properties through said aperture and changing said aperture for successive tests, $D_m$ is a minimum aperture size such that $D_m \geq 3 d_s$, $d_s$ is the average grain size, $d_o$ is a measure of aperture diameter, $\rho_s$ is the density of the solid granular material, A is a known cross section of a particular aperture, g is the gravitational acceleration constant, j is a coefficient of rolling-sliding substance, G is a coefficient of material quality representing granule shape and $\rho$ is the virtual density of the aggregated material, coefficients j and G being determined by passage of a material with given properties through said aperture changing said aperture for successive tests;

(j) outputting at least one result signal representing at least one of flow properties of said sample by the processing of the signals applied to said unit in accordance with a least one of the relationships for Q and Q/A, respectively, and (k) regulating a filling apparatus to reproducibly fill a granular material with unknown properties but corresponding values of said constants and coefficients into a receptacle therefor.

* * * * *